United States Patent [19]

Bolich, Jr.

[11] Patent Number: 4,874,868

[45] Date of Patent: Oct. 17, 1989

[54] VOLATILE SILICONS

[75] Inventor: Raymond E. Bolich, Jr., Maineville, Ohio

[73] Assignee: The Procter & Gamble Company, Cincinnati, Ohio

[21] Appl. No.: 168,720

[22] Filed: Mar. 16, 1988

[51] Int. Cl.$^4$ .......................... C07F 7/10; C07F 7/08
[52] U.S. Cl. .................................. 548/110; 548/406; 556/437; 556/460; 556/445
[58] Field of Search ............... 556/419, 437, 460, 445, 556/400; 548/406; 536/425

[56] References Cited

U.S. PATENT DOCUMENTS

| | | | |
|---|---|---|---|
| 2,416,504 | 2/1943 | Troutman et al. | 556/460 |
| 2,891,980 | 6/1959 | Gilbert et al. | 556/460 |
| 4,075,167 | 2/1978 | Takamizawa et al. | 548/406 |
| 4,154,619 | 5/1979 | Pronk . | |
| 4,207,424 | 6/1980 | Winnick . | |
| 4,355,062 | 10/1982 | Wang et al. . | |
| 4,364,837 | 12/1982 | Pader . | |
| 4,376,087 | 3/1983 | Poliniak et al. . | |
| 4,391,720 | 7/1983 | Wang et al. . | |
| 4,462,921 | 7/1984 | Peterson et al. . | |
| 4,472,337 | 9/1984 | Huck et al. . | |

OTHER PUBLICATIONS

Ser. No. 168,725, 03001988, Bolich, Jr.

Primary Examiner—Paul F. Shaver
Assistant Examiner—Stuart L. Hendrickson
Attorney, Agent, or Firm—Douglas C. Mohl; Steven J. Goldstein; David K. Dabbiere

[57] ABSTRACT

Novel volatile silicon compounds are disclosed which are very suitable for use in cosmetic and household products.

2 Claims, No Drawings

VOLATILE SILICONS

BACKGROUND OF THE INFORMATION

Volatile silicons have found wide acceptance in a number of different types of products ranging from cosmetics to antifreeze formulations. Such silicons are good solvents for a variety of materials and serve to give excellent feel on surfaces such as skin and hair.

The most common types of volatile silicons are linear and cyclic siloxanes having from one to about seven siloxane groups. While these are the most common, there are other types which have been disclosed. Included among such other silicons are those in U.S. Pat. No. 4,207,424, June 10, 1980 to Winnick

and

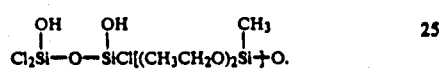

Additional disclosures of volatile silicons are in U.S. Pat. No. 4,355,062, Oct. 19, 1982 to Wang et al. Certain alkyl linear siloxanes such as

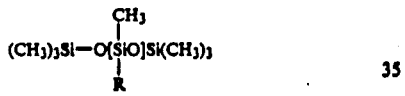

are disclosed in U.S. Pat. No. 4,376,087, Mar. 8, 1983 to Poliniak et al. Cyclic silicones different from those mentioned above are disclosed in U.S. Pat. No. 4,364,837, Dec. 21, 1982 to Pader. Still other volatile silicons are disclosed in Japanese unexamined applications JP 9108-046, Oct. 14, 1974; JP 1102-019, Sept. 7, 1976; JP 607-824, June 15, 1981; JP 6139-527, Oct. 31, 1981; and JP 7035-526, Feb. 26, 1982.

Although the references discussed above disclose a variety of volatile silicons, there is still the need for additional materials which meet the requirements of cosmetic and household products.

It is therefore an object of the present invention to provide novel volatile silicon compounds.

It is a further object to provide novel silicon compounds which have good solvency properties.

It is a further object of the present invention to provide noel silicon compounds which have good compatibility with conventional cosmetic and household product ingredients.

These and other objectives will become readily available from the detailed disclosure below.

All percentages and ratios here are by weight unless otherwise specified. Additionally, all measurements are made at 25° C. unless otherwise specified.

SUMMARY OF THE INVENTION

The present invention relates to novel silicon compounds of the following structures:

(a) Linear siloxanes

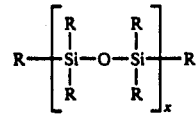

where (1) $X = 1$ to 4, (2) total carbons $\leq 14$, (3) R can be independently $C_1$–$C_{10}$ alkyl, trialkyl siloxy and (4) at least one R per molecule must be selected from $R_1 R_2$ where $R_1 = C_1$–$C_4$ alkylene and $R_2 = -O-R_3$ wherein $R_3 = C_1$–$C_5$ alkyl or $-C_1$–$C_7$ ketone or $R_2 =$

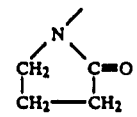

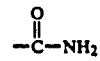

or

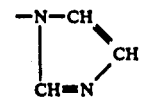

(b) Cyclic siloxanes

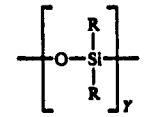

where (1) $Y = 3$ to 6, (2) total carbons $\leq 14$, (3) R can be independently $C_1$–$C_{10}$ alkyl and (4) at least one R per molecule must be selected from $-R_1 R_2$ where $R_1 = C_1$–$C_4$ alkylene and $R_2 = $(i) $-O-R_3$, where $R_3 = C_1$–$C_5$ alkyl, (ii) $C_1$–$C_7$ ketone,

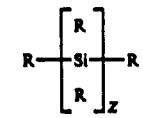

(c) Silanes

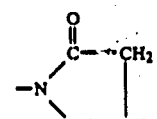 (iii)

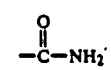 (iv)

-continued (v)

$$\underset{\underset{N}{\overset{HC}{\underset{\parallel}{\bigvee}}}\overset{N}{\underset{CH}{\overset{\diagup}{\diagdown}}}CH,}{\underset{CH}{\overset{N}{\diagdown}}}$$ and (vi)

$$-\overset{O}{\overset{\parallel}{C}}-OH.$$

where (1) $Z = 1$ to 4, (2) total carbons $\leq 14$, (3) R can be independently $C_1$-$C_{10}$ alkyl, trialkyl ($C_1$-$C_3$) siloxy and (4) at least one R per molecule must be selected from $-R_1 R_2$ where $R_1 = C_1$-$C_4$ alkylene and $$R_2 = -\overset{O}{\overset{\parallel}{C}}-NH_2$$

or $$\underset{CH_2-CH_2}{\overset{N}{\underset{CH_2}{\diagup}}\overset{\diagdown}{C=O}}$$

or $$\underset{\underset{N}{CH}\overset{\diagup}{\underset{\parallel}{\diagdown}}\overset{N}{\underset{CH}{\diagup}}CH}{}$$

or $-CN$ or $-C_1$-$C_7$ ketone

*The boiling point of all of these novel silicon compounds at 760 mm is $\leq 260°$ C.

DETAILED DESCRIPTION OF THE INVENTION

The present invention as summarized above relates to novel silicon compounds which find use in cosmetic and household products. Specifically, the silicon compounds are novel linear siloxanes (a) cyclic siloxanes (b) and silanes (c).

Examples of these materials include, among many others, the following:

A $$CH_3-\underset{\underset{O}{|}}{\overset{CH_3}{\underset{|}{Si}}}-O-\underset{\underset{O}{|}}{\overset{CH_3}{\underset{|}{Si}}}-CH_3$$
$$CH_3-\underset{\underset{CH_3}{|}}{\overset{|}{Si}}-O-\underset{\underset{CH_3}{|}}{\overset{|}{Si}}-C_2H_4-OCH_3,$$

B $$CH_3-\underset{\underset{CH_3}{|}}{\overset{CH_3}{\underset{|}{Si}}}-O-\underset{\underset{CH_3}{|}}{\overset{CH_3}{\underset{|}{Si}}}-C_2H_4-\underset{\underset{CH_2-CH_2}{|}}{\overset{\overset{O}{\underset{\parallel}{C}}-CH_2}{N}}$$

C $$\underset{CH_3}{\overset{CH_3}{\diagdown}}\overset{CH_3}{\underset{\diagup}{Si}}$$
$$CH_3-\underset{\underset{CH_3}{|}}{\overset{O}{\underset{|}{Si}}}\overset{O}{\underset{|}{\diagdown}}\underset{\underset{CH_3}{|}}{\overset{O}{\underset{|}{Si}}}-CH_2CH_2-\overset{O}{\overset{\parallel}{C}}-NH_2$$

and

D $$CH_3-\underset{\underset{CH_3}{|}}{\overset{CH_3}{\underset{|}{Si}}}-O-\underset{\underset{CH_3}{|}}{\overset{CH_3}{\underset{|}{Si}}}-C_4H_8-\overset{O}{\overset{\parallel}{C}}-C_2H_5$$

The novel silicon compounds find use in a variety of cosmetic and household products. Components of such products are set forth in the following paragraphs.

Hair Care Products

The hair care products using the novel silicons of the present invention contain the volatile silicon compound along with a carrier benefiting from the silicon compound. The term "carrier", as used herein, means one or more compatible vehicles which are suitable for administration to the hair of a human or lower animal. The term "compatible", as used herein, means that the components of the carrier are capable of being commingled with the novel silicon of the present invention, and with each other, in a manner such that there is no interaction which would substantially reduce the ability of the hair care products to provide its benefit under ordinary use situation.

Carriers suitable for use with the volatile silicon agent such as shampoos and cream rinse conditioners to hair are well known in the art, and their selection can be made without difficulty by a person skilled in the art. For example, carriers which are suitable are described in more detail in U.S. Pat. No. 3,477,517, to Kubot et al, issued May 4, 1971; U.S. Pat. No. 3,907,984, to Calvert et al, issued Sept. 23, 1975; U.S. Pat. No. 4,012,501, to Farber, issued Mar. 15, 1977; U.S. Pat. No. 4,223,009, to Chakrabarti, issued Sept. 16, 1980; and U.S. Pat. No. 4,283,384, to Jacquet et al, issued Aug. 11, 1981; the disclosures of all these patents being incorporated herein by reference in their entirety.

Shampoo compositions useful with the novel silicons of this invention utilize conventional components. The shampoos comprise from about 0.1% to about 20% of the volatile silicon; from about 5% to about 60% of a synthetic surfactant; and the balance water. Suitable surfactants include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, lauryl sarcosine, cocoyl sarcosine, ammonium cocoyl sulfate, ammonium lauryl sulfate, sodium cocoyl sulfate, sodium lauryl sulfate, potassium cocoyl sulfate, potassium lauryl sulfate, triethanolamine lauryl sulfate, triethanolamine lauryl sulfate, monoethanolamine cocoyl sulfate, monethanolamine lauryl sulfate, sodium tridecyl benzene sulfonate and sodium dodecyl benzene sulfonate.

Shampoos can also contain a variety of nonessential optional components. Such conventional optional ingredients are well known to those skilled in the art, e.g., preservatives, such as benzyl alcohol, ethyl paraben, propyl paraben and imidazolidinyl urea; hair setting/styling polymers such as acrylate polymers and copolymers, cationic surfactants, such as cetyl trimethyl ammonium chloride, lauryl trimethyl ammonium chloride, tricetyl methyl ammonium chloride, stearyldimethyl benzyl ammonium chloride, and di(partially hydrogenated tallow) dimethylammonium chloride; thickeners and viscosity modifiers such as a diethanolamide of a long-chain fatty acid (e.g. PEG 3 lauramide), block polymers of ethylene oxide and propylene oxide, sodium chloride, sodium sulfate, polyvinyl alcohol, ethyl alcohol and water-soluble polymers such as xanthan gum, hydroxyethyl cellulose, guar gum and starch; pH adjusting agents, such as citric acid, succinic acid, phosphoric acid, sodium hydroxide, sodium carbonate; perfumes; dyes; and, sequestering agents, such as disodium ethylenediamine tetraacetate. Such agents generally are used individually at a level of from about 0.01% to about 10%, preferably from about 0.5% to about 5.0% by weight of the composition.

Another carrier useful with the present silicons are creme rinses/conditioners. Such a carrier preferably comprises two essential components: a lipid vehicle material and generally a cationic surfactant vehicle material. Such carriers are generally described in the following documents, all incorporated by reference herein: Barry, "The Self Bodying Action of the Mixed Emulsifier Sodium Dodecyl Sulfate/Cetyl Alcohol", 28 J. of Colloid and Interface Science 82–91 (1968); Barry, et al., "The SelfBodying Action of Alkyltrimethylammonium Bromides/Cetostearyl Alcohol Mixed Emulsifiers; Influence of Quaternary Chain Length", 35 J. of Colloid and Interface Science 689–708 (1971); and Barry, et al., "Rheology of Systems Containing Cetomacrogol 1000 - Cetostearyl Alcohol, I. Self Bodying Action", 38 J. of Colloid and Interface Science 616–625 (1972).

Lipid Materials include naturally or synthetically-derived acids, acid derivatives, alcohols, esters, ethers, ketones, and amides with carbon chains of from 12 to 22, preferably from 16 to 18, carbon atoms in length. Fatty alcohols and fatty esters are preferred; fatty alcohols are particularly preferred.

Lipid materials among those useful herein are disclosed in Bailey's Industrial Oil and Fat Products, (3d edition, D. Swern, ed. 1979) (incorporated by reference herein). Fatty alcohols included among those useful herein are disclosed in the following documents, all incorporated by reference herein: U.S. Pat. No. 3,155,591, Hilfer, issued Nov. 3, 1964; U.S. Pat. No. 4,165,369, Watanabe, et al., issued Aug. 21, 1979; U.S. Pat. No. 4,369,824, Villamarin, et al., issued May 26, 1981; British Specification 1,532,585, published Nov. 15, 1978; and Fukushima, et al, "The Effect of Cetostearyl Alcohol in Cosmetic Emulsions", 98 Cosmetics & Toiletries 89–102 (1983). Fatty esters included among those useful herein disclosed in U.S. Pat. No. 3,341,465, Kaufman, et al., issued Sept. 12, 1967 (incorporated by reference herein).

Preferred esters for use herein include cetyl palmitate and glycerylmonostearate. Cetyl alcohol and stearyl alcohol are preferred alcohols. A particularly preferred lipid vehicle material is comprised of a mixture of cetyl alcohol and stearyl alcohol containing from about 55% to about 65% (by weight of mixture) of cetyl alcohol.

Deodorant/Antiperspirants

Deodorant/antiperspirant compositions utilizing the volatile silicons include a variety of components.

Antiperspirant Actives

Antiperspirant compositions comprise at least one antiperspirant active. Antiperspirant actives useful in the present invention are well known in the art, and are disclosed generally in Miller and Hoag, "Personal Care Products", Handbook of Nonprescription Drugs, 8th Edition, Chapter 19, pages 397–417 (American Pharmaceutical Association; 1986), the disclosures of which are incorporated herein by reference in their entirety. Antiperspirant actives useful herein are also more specifically disclosed in European Patent Application Publication No. 28,853, published May 20, 1981, by Beckmeyer et al.; and European Patent Application Publication No. 117,070, published Aug. 29, 1984, by May, the disclosures of both these patent specifications being incorporated herein by reference in their entirety. Antiperspirant actives include, for example, aluminum chlorohydrates, aluminum chloride, sodium aluminum chlorohydroxy lactate, buffered aluminum sulfate, and aluminum zirconium chlorohydrates.

Preferred are astringent metallic salts including the inorganic and organic salts of aluminum, zirconium and zinc, and mixtures thereof. Particularly preferred are the aluminum and zirconium salts, such as aluminum halides, aluminum hydroxyhalides, zirconyl oxyhalides, zirconyl hydroxyhalides, and mixtures thereof. Such metal salts, and complexes thereof, are described in European Patent Specification Publication No. 117,070, to May, published Aug. 29, 1984, and U.S. Pat. No. 4,137,306, to Rubino et al., issued Jan. 30, 1979, the disclosures of both these patent specifications being incorporated herein by reference in their entirety.

Preferred aluminum salts include those of the formula:

wherein a is from about 2 to about 5; a+b=6; x is from about 1 to about 6; and wherein a, b, and x may have non-integer values. Particularly preferred are aluminum chlorhydroxides referred to as "5/6 basic chlorhydroxide", wherein a=5; and "⅔ basic chlorhydroxide", wherein a=4. Processes for preparing aluminum salts are disclosed in the following documents all incorporated by reference herein in their entirety: U.S. Pat. No. 3,887,692, to Gilman, issued June 3, 1975; U.S. Pat. No. 3,904,741, to Jones et al., issued Sept. 9, 1975; U.S. Pat. No. 4,359,456, to Gosling et al., issued Nov. 16, 1982; and British Patent Specification 2,048,229, to Fitzgerald et al., published Dec. 10, 1980. Mixtures of aluminum salts are described in British Patent Specification 1,347,950, to Shin et al., published Feb. 27, 1974, the disclosures of which are incorporated herein by reference in their entirety.

Zirconium salts are also preferred for use in antiperspirant compositions of the present invention. Such salts are of the general formula:

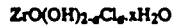

where a is from about 1 to about 2, preferably from about 1.5 to about 1.87; x is from about 1 to about 7; and wherein a and x may have non-integer values. These zirconium salts are disclosed in Belgium Patent Specification 825,146, to Schmitz, issued Aug. 4, 1975, the disclosures of which are incorporated herein by reference in their entirety. Particularly preferred zirconium salts are those complexes also containing aluminum and glycine, commonly known as "ZAG complexes". Such ZAG complexes contain aluminum chlorhydroxide and zirconyl hydroxychloride of the formulae detailed above. These compounds in ZAG complexes are disclosed in the following patent documents, all incorporated by reference herein in their entirety: U.S. Pat. No. 2,814,585 to Daley, issued Nov. 26, 1957; U.S. Pat. No. 3,679,068, to Luedders et al., issued Feb. 12, 1974; U.S. Pat. No. 4,017,599, to Rubino, issued Apr. 12, 1977; U.S. Pat. No. 4,120,948, to Shelton, issued Oct. 17, 1978; and British Patent Specification 2,144,992, to Callaghan et al., published Mar. 20, 1985.

The antiperspirant actives in total typically comprise from about 1% to about 50% by weight of the composition of the present invention, more preferably from about 5% to about 40%, and most preferably from about 5% to about 30%.

Deodorant/Antiperspirant Carrier

The selection of carriers for use with the volatile silicons of the present invention is readily made by one skilled in the art based on the form of the composition being prepared, for example, aerosol spray, roll-on lotion, or stick. Antiperspirant carriers are described in detail in European Patent Application Publication No. 28,853, published May 20, 1981, by Beckmeyer et al.; and European Patent Application Publication No. 117,070, published Aug. 29, 1984, by May; the disclosures of both these patent specifications being incorporated herein by reference in their entirety. Carrier materials suitable for use for various composition forms are also described in detail as follows:

(i) Stick Antiperspirant Carriers

Antiperspirant compositions in stick form contain the volatile silicon, which may function as a liquid emollient and preferably contain one or more non-volatile emollients. Such materials include fatty acid and fatty alcohol esters, water-insoluble ethers and alcohols, polyorganosiloxanes, and mixtures thereof. Emollients among those useful herein are described in *Cosmetics, Science and Technology* 27–104 (M. Balsam and E. Sagarin ed. 1972), and U.S. Pat. No. 4,202,879, to Shelton, issued May 13, 1980 (both incorporated by reference herein).

The present compositions in stick form preferably contain a non-volatile silicone oil as an emollient material. Such silicone oils include polyalkylsiloxanes, polyalkylarylsiloxanes, and polyethersiloxane copolymers. The essentially non-volatile polyalkyl siloxanes useful herein include, for example, polydimethyl siloxanes with viscosities of from about 5 to about 100,000 centistokes at 25° C. Among the preferred non-volatile emollients useful in the present compositions are the polydimethyl siloxanes having viscosities from about 10 to about 400 centistokes at 25° C. Such polyalkyl siloxanes include the Vicasil series (sold by General Electric Company) and the Dow Corning 200 series (sold by Dow Corning Corporation). Polyalkylaryl siloxanes include poly methylphenyl siloxanes having viscosities of from about 15 to about 65 centistokes at 25° C. These are available, for example, as SF 1075 methylphenyl fluid (sold by General Electric Company) and 556 Cosmetic Grade Fluid (sold by Dow Corning Corporation). Useful polyether siloxane copolymers include, for example, a polyoxyalkylene ether copolymer having a viscosity of about 1200 to 1500 centistokes at 25° C. Such a fluid is available as SF-1066 organosilicone surfactant (sold by General Electric Company). Polysiloxane ethylene glycol ether copolymers are preferred copolymers for use in the present compositions.

Antiperspirant compositions in stick form further preferably contain one or more materials having waxlike characteristics and having a melting point of from about 65° C. to about 102° C. Such waxes include beeswax, spermaceti, carnauba, baysberry, candelilla, montan, ozokerite, ceresin, paraffin, hydrogenated castor oil (castor wax), synthetic waxes such as Fisher-Tropsch waxes, microcrystalline wax, and mixtures thereof. Castor wax is a preferred high-melting point wax useful herein. Such high-melting point waxes among those useful herein are disclosed in U.S. Pat. No. 4,049,792, to Elsnau, issued Sept. 20, 1977 (incorporated by reference herein).

(ii) Aerosol Spray Deodorant/Antiperspirant Carriers

The present compositions in aerosol spray form preferably contain one or more volatile materials, herein "aerosol propellants", which in a gaseous state, carry the other components of the spray composition in particulate or droplet form. The aerosol propellants useful in the present invention typically have a boiling point within the range of from about −45° C. to about 5° C. The aerosol propellants are liquified when packaged in conventional aerosol containers under pressure. The rapid boiling of the aerosol propellant upon leaving the aerosol container aids in the atomization of the other components of the present invention.

Aerosol propellants useful in the compositions of the present invention in spray form include those well known in the art. Such aerosol propellants include the chemically-inert hydrocarbons such as propane, n-butane, isobutane and cyclopropane, and mixtures thereof, as well as halogenated hydrocarbons such as dichlorodifluoromethane (propellant 12), 1,1-dichloro-1,1,2,2tetrafluoroethane (propellant 140, 1-chloro-1,1-difluoro-2,2trifluoroethane (propellant 115), 1-chloro-1,1-difluoroethylene (propellant 142B), 1,1-difluoroethane (propellant 152A), and monochlorodifluoromethane, and mixtures thereof. Isobutane, used singly or admixed with other hydrocarbons, is preferred for use in the present aerosol spray antiperspirants.

Another preferred material for use in the aerosol compositions in aerosol spray form is a silicone gum. As referred to herein, "Silicone gum" materials useful in the present compositions are those non-functionalized siloxanes having a viscosity of from about 500,000 to about 100,000,000 centistokes at 25° C. These materials are incorporated in the present compositions at a level of from about 0.05% to about 5.0%, preferably from about 0.10% to about 2.0%. Preferred silicone gums include linear and branched polydimethyl siloxanes, of the following general formula:

$$(CH_3)_3SiO-[Si(CH_3)_2O]_n-Si(CH_3)_3$$

wherein n is from about 2,000 to about 15,000, preferably from about 2,000 to about 7,000. The silicone gums useful herein may also be substituted with non-electronegative substituents. Silicone gums among those useful herein are available from a variety of commercial sources, including X2-1346 and Dow Corning 200 Fluid (manufactured by Dow Corning Corporation), PS240 (manufactured by Petrarch Systems, Inc.), and SE76, SE30 and SE32 Silicone Gums (manufactured by General Electric Company).

The aerosol compositions may also contain a bulking or suspending agent, at levels of from about 0.1% to about 7%, preferably from about 0.4% to about 3.5%. Such bulking/suspending agents include talc, colloidal silicas, clays and mixtures thereof. Clays and colloidal silicas are particularly preferred. Clay bulking/suspending agents include montmorillonite clays and hydrophobically treated montmorillonites, e.g., bentonites, hectorites and colloidal magnesium aluminum silicates. These materials are available from a variety of sources, including Laponite hectorite (sold by Laponite Industries, Ltd.) and Veegum magnesium aluminum silicate (sold by R. T. Vanderbilt Co.). A preferred clay bulking/suspending agent is hydrophobically-tre montmorillonite, such as the Bentone bentonites (sold by NL Industries, Inc.). Colloidal silicas are also readily available, such as Cab-O-Sil pyrogenic colloidal silica (sold by Cabot Corporation).

(iii) Roll-on Lotion Deodorant/Antiperspirant Carriers

Antiperspirant/deodorant compositions of the present invention in roll-on lotion form typically comprise carrier materials similar to those utilized in aerosol spray forms except that no aerosol propellant is required. Antiperspirant/deodorant compositions in roll-on lotion form, and carrier materials useful therein, are described in detail in European Patent Application Publication No. 28,853, published May 20, 1981, by Beckmeyer et al., the disclosures of which are incorporated herein by reference in their entirety.

Additional active components include bacteriostats and fungistats. The particular non-active components that may be useful will depend upon the form of application that is desired. Such components include, for example, emollients, colorants, perfumes, and emulsifiers. Optional components useful herein are described in the following documents, all incorporated by reference herein: U.S. Pat. No. 4,049,792, to Elsnau, issued Sept. 20, 1977; Canadian Pat. No. 1,164,347, to Beckmeyer, et al., issued Mar. 27, 1984; European Patent Specification 117,070, to May, published Aug. 29, 1984; and Geria, "Formulation of Stick Antiperspirants and Deodorants," 99 *Cosmetics & Toiletries* 55-60 (1984).

Generally, the deodorant/antiperspirant carriers in total comprise from about 40% to about 99% by weight of the compositions of the present invention, preferably from about 55% to about 95%, and most preferably from about 67% to about 94%.

METHOD OF MANUFACTURE OF VOLATILE SILICONS

The novel silicon compounds of the present invention can be prepared by a number of different synthetic routes which are well known and broadly used by workers skilled in the art.

Linear Siloxane Derivatives

These compounds are usually prepared from two reactions. A hydrosilylation reaction between dimethylchloro silane and an olefinic functional molecule is the first step. This is done between 60°-100° C. for 5-20 hours in the presence of a peroxide and/or U.V. light. The resultant product is distilled to remove impurities. The distillate is then hydrolyzed with trimethyl chloro silane (and optionally with a third reactant, dimethyl dichloro silane). This reaction is carried out with excess water and usually HCl as catalyst. The resultant product is an oily layer on top of the water. This oily phase is distilled to isolate and purify the novel compound. The chart below exemplifies precursors used for some of the novel linear siloxane compounds.

| Silane | Olefinic Compound | Novel Linear Silicone |
|---|---|---|
| dimethyl chloro silane | methyl allyl ether | $CH_3-Si(CH_3)_2-O-Si(CH_3)_2-C_3H_6OCH_3$ |
| dimethyl chloro silane | vinyl imidazol | $CH_3-Si(CH_3)_2-O-Si(CH_3)_2-C_2H_4-N$(imidazolyl) |

Cyclic Siloxane Derivatives

The synthetic route and reaction conditions for these are very similar to the linear materials. There are differences. In the hydrosilylation step, methyl dichloro silane (or other alkyl dichloro silane) is used in place of the dimethyl chloro silane. In the hydrolysis step, the co-reactant is dimethyl dichloro silane rather than trimethyl chloro silane. The resultant products are cyclic. The chart below exemplifies precursors used for some of the novel cyclic siloxane compounds.

| Silane | Olefinic Compound | Novel Cyclic Silicone |
|---|---|---|
| methyl dichloro silane | ethyl vinyl ketone | $CH_3-Si(CH_3)(O-)-O-Si(CH_3)(O-)-C_2H_4CC_2H_5$ ; $CH_3-Si(CH_3)-O-Si(CH_3)-CH_3$ |
| methyl dichloro silane | butyl vinyl ether | $CH_3-Si(CH_3)(O-)-O-Si(CH_3)(O-)-C_2H_4-O-C_4H_9$ ; $CH_3-Si(CH_3)-O-Si(CH_3)-CH_3$ |

Silane Derivative

Silanes are prepared by reacting a commercially available hydrosilane with the appropriate commercially available olefinic functional molecule. This is usually done at 60°-100° C. for 5-20 hours in the presence of a peroxide (such a acetyl peroxide) and/or UV light. The resultant product of this reaction is distilled to isolate the desired compound from impurities. The chart below exemplifies precursors used for some of the novel compounds.

| | Precursors | |
|---|---|---|
| Silane | Olefinic Compound | Novel Silane |
| trimethyl silane | acryl-amide | 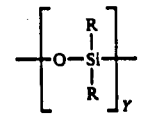 |
| trimethyl silane | vinyl pyrolidone | CH₃—Si(CH₃)(CH₃)—C₂H₄—N(CH₂—CH₂)(C(=O)—CH₂) |

The following nonlimiting examples of the present invention are given solely for illustration and are not to be construed as limitations of this invention. As many variations are possible without departing from the spirit and scope thereof.

EXAMPLE I

The following is a highlighting rinse representative of the present invention.

| Component | Weight % |
|---|---|
| D & C Red #17 | 0.10 |
| Volatile Silicone A[4] | 5.00 |
| Cetyl Alcohol | 2.00 |
| Ditallow Dimethyl Ammonium Chloride | 1.00 |
| Ceteareth-20 | 1.00 |
| Kathon CG | .04 |
| Double Reverse Osmosis Water | q.s. |

EXAMPLE II

The following is a shampoo representative of the present invention.

| Component | Weight % |
|---|---|
| Ammonium Lauryl Sulfate | 15.00 |
| Jaguar HP-60[1] | 1.00 |
| G.E. SE 30[2] | 1.00 |
| Volatile Silicone D[4] | 1.00 |
| Kathon CG[3] | .04 |
| Double Reverse Osmosis Water | q.s. |

[1] Hydroxypropyl guar gum offered by Hi-tek Polymers Inc.
[2] Silicone gum offered by General Electric.
[3] Offered by Rohm and Haas.
[4] Volatile silicon compounds as identified on page 4.

What is claimed is:

1. A volatile silicon compound having the structure:

$$\left[ -O-\underset{\underset{R}{|}}{\overset{\overset{R}{|}}{Si}}- \right]_Y$$

where (1) $Y = 3$ to 6, (2) total carbons $\leq 14$, (3) R can be independently $C_1$-$C_{10}$ alkyl and (4) at least one R per molecule must be selected from - $R_1$ $R_2$ where $R_1 = C_1$-$C_4$ alkylene and $R_2$ is selected from the group consisting of (i) —O—$R_3$ where $R_3 = C_1$-$C_5$ alkyl, (ii) -$C_1$-$C_7$ ketone,

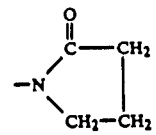 (iii)

 (iv)

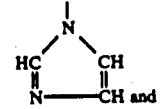 (v)

 and $$-\overset{\overset{O}{\|}}{C}-OH. \quad (vi)$$

2. A volatile silicon compound having the formula:

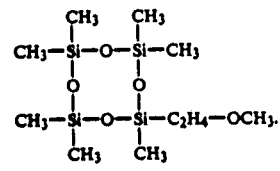

* * * * *

UNITED STATES PATENT AND TRADEMARK OFFICE
CERTIFICATE OF CORRECTION

PATENT NO. : 4,874,868

DATED : October 17, 1989

INVENTOR(S) : Raymond E. Bolich, Jr.

It is certified that error appears in the above-identified patent and that said Letters Patent is hereby corrected as shown below:

Delete in column 2, lines 50 - 57.

Column 3, line 11 insert:

c) Silanes

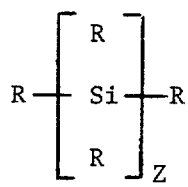

Column 4, line 40, 3,477,517 should read "3,577,517."

Column 5, line 55, 4,369,824 should read "4,269,824."

Signed and Sealed this

Fourteenth Day of December, 1993

Attest:

BRUCE LEHMAN

*Attesting Officer*      *Commissioner of Patents and Trademarks*